(12) United States Patent
Hoshino et al.

(10) Patent No.: US 7,371,547 B2
(45) Date of Patent: May 13, 2008

(54) PROCESS FOR PRODUCING VITAMIN B6

(75) Inventors: Tatsuo Hoshino, Kanagawa-ken (JP);
Yoichiro Nagatani, Kanagawa-ken (JP);
Keiko Ichikawa, Kanagawa-ken (JP);
Masaaki Tazoe, Kanagawa-ken (JP)

(73) Assignee: DSM IP Assets B.V., Heerlen (NL)

( * ) Notice: Subject to any disclaimer, the term of this patent is extended or adjusted under 35 U.S.C. 154(b) by 173 days.

(21) Appl. No.: 10/528,892

(22) PCT Filed: Sep. 16, 2003

(86) PCT No.: PCT/EP03/10296

§ 371 (c)(1),
(2), (4) Date: Mar. 23, 2005

(87) PCT Pub. No.: WO2004/029270

PCT Pub. Date: Aug. 4, 2004

(65) Prior Publication Data

US 2006/0216798 A1    Sep. 28, 2006

(30) Foreign Application Priority Data

Sep. 27, 2002    (EP) ................... 02021601

(51) Int. Cl.
*C12P 17/12* (2006.01)
*C12N 9/02* (2006.01)
*C12N 1/20* (2006.01)
*C07K 1/00* (2006.01)
*C07H 21/04* (2006.01)

(52) U.S. Cl. ............... 435/122; 435/41; 435/183; 435/189; 435/252.3; 435/320.1; 530/350; 536/23.2

(58) Field of Classification Search ............... 435/41, 435/122, 183, 189, 252.3, 320.1; 530/350; 536/23.2
See application file for complete search history.

(56) References Cited

FOREIGN PATENT DOCUMENTS

EP    0 765 938 A2    4/1997
EP    0 950 715 A2    10/1999

OTHER PUBLICATIONS

Laber et al. FEBS Lett. 1999 Apr. 16;449(1):45-8.*
Tazoe, M. et al., "Production of Vitamin $B_6$ in Rhizobium," *Biosci. Biotechnol. Biochem.*, vol. 63, No. 8, pp. 1378-1382 (1999).
Tazoe, M. et al., "Biosynthesis of Vitamin $B_6$ in Rhizobium," *J. Biol. Chem.*, vol. 275, No. 15, pp. 11300-11305 (2000).
Laber, B. et al., "Vitamin $B_6$ biosynthesis: formation of pyridoxine 5'-phosphate from 4-(phosphohydroxy)-L-threonine and Ideoxy-D-xylulose-5-phosphate by PdxA and PdxJ Protein," *FEBS Letters*, vol. 449, pp. 45-48 (1999).
Tazoe, M. et al., "Biosynthesis of Vitamin $B_6$ in Rhizobium: In Vitro Synthesis of Pyridoxine 1-Deoxy-D-xylulose and 4-Hydroxy-L-threonine," *Biosci. Biotechnol. Biochem*, vol. 66, No. 4, pp. 934-936 (2002).
Capela, D. et al., "Analysis of the Chromosome Sequence of the Legume Symbiont Sinorhizobium meliloti Strain 1021." *Proc. Natl. Acad. Sci.*, vol. 98, No. 17, pp. 9877-9882 (2001).
Galibert, F. et al., "The Composite Genome of the Legume Symbiont Sinorhizobium meliloti," *Science*, vol. 293, pp. 668-672 (2001).
Mittenhuber, G., "Phylogenetic Analyses and Comparative Genomics of Vitamin $B_6$ (Pyridoxine) and Pyridoxal Phosphate Biosynthesis Pathways," *J. Mol. Microbiol. Biotechnol.*, vol. 3, No. 1, pp. 1-20 (2001).
Capela, D. et al., "Analysis of the Chromosome sequence of the legume symbiont Sinorhizobium meliloti Strain 1021," *Proc. Natl. Acad. Sci*, vol. 98, No. 17, pp. 9877-9882 (2001), NCBI Database Abstract No. XP-002272564.
Galibert, F. et al., "The Composite Genome of the Legume Symbiont Sinorhizobium meliloti," *Science*, vol. 293, pp. 668-672 (2001), NCBI Database Abstract No. XP-002272565.

* cited by examiner

*Primary Examiner*—Tekchand Saidha
*Assistant Examiner*—Christian L. Fronda
(74) *Attorney, Agent, or Firm*—Bryan Cave LLP

(57) ABSTRACT

Disclosed is a mutant of a recombinant microorganism of the genus *Sinorhizobium* capable of producing vitamin $B_6$ having a recombinant plasmid with pdxJ gene that acquired histidine requirement of glycine resistance, or its combination thereof.

6 Claims, 1 Drawing Sheet

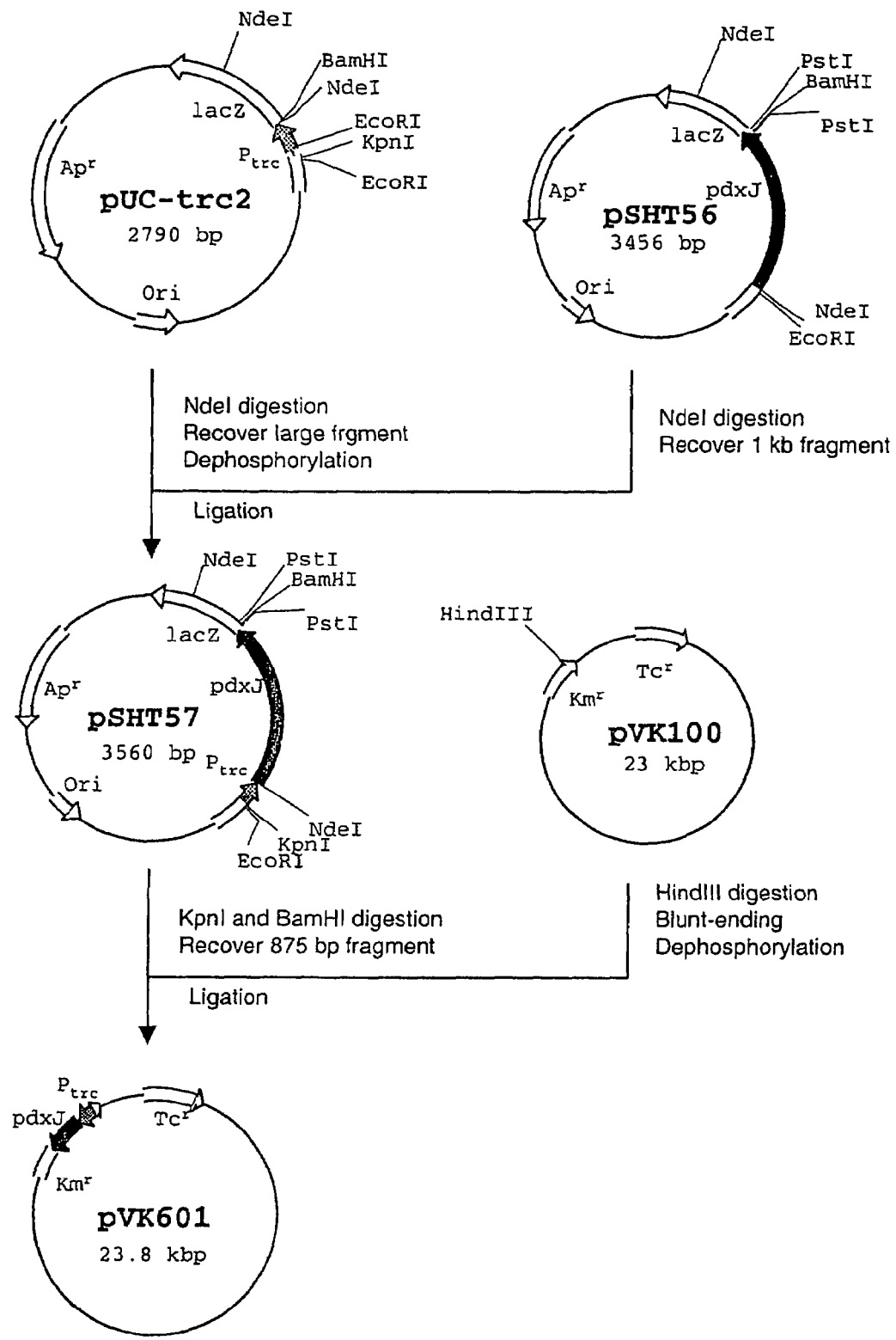
Fig. 1 The construction of a recombinant plasmid pVKP601

PROCESS FOR PRODUCING VITAMIN B6

This application is the National Stage of International Application No. PCT/EP2003/010296, filed Sep. 16, 2003.

The present invention relates to a novel microorganism and a process for preparing vitamin $B_6$ by using the same.

"Vitamin $B_6$" as used in the present invention includes pyridoxol, pyridoxal, and pyridoxamine. Vitamin $B_6$ is a vitamin indispensable to human beings or other animals and used as a raw material of medicines or as feed additives. As a process for preparing vitamin $B_6$ in a fermentation method, a process for preparing vitamin $B_6$ using a microorganism derived from the genus *Sinorhizobium* (also known as *Rhizobium*) (EP 765,938) is known. But it is necessary to construct a new microorganism with a higher yield of vitamin $B_6$ and lo to develop an improved industrial fermentation process which can produce vitamin $B_6$ with sufficiently high production efficiency using said microorganism.

According to the present invention, it is possible to produce vitamin $B_6$ more efficiently than the previous process. The present inventors first constructed a recombinant micro-organism of the genus *Sinorhizobium* capable of producing vitamin $B_6$ incorporated with a recombinant plasmid comprising a vector containing pyridoxol 5'-phosphate synthase gene (referred to as pdxJ hereinafter). This recombinant microorganism showed an increased production of vitamin $B_6$. This recombinant microorganism was further mutated to acquire a phenotypic property of histidine requirement, or glycine resistance. Such a mutant microorganism shows further increased productivity of vitamin $B_6$. A mutant which acquired the above mentioned two phenotypic properties simultaneously shows drastically increased productivity of vitamin $B_6$, and that vitamin $B_6$ can advantageously be produced in the culture broth by cultivating the microorganism, and can be recovered therefrom in a desired purity.

The present invention provides a mutant of a recombinant microorganism of the genus *Sinorhizobium* capable of producing vitamin $B_6$ having a recombinant plasmid with pdxJ gene that acquired a phenotypic property of histidine requirement or glycine resistance, or combination of the phenotypic properties thereof.

Another object of the present invention is to provide a process for preparing vitamin $B_6$ which comprises cultivating said microorganism in a culture medium and collecting the produced vitamin $B_6$.

As a parent strain for preparing a microorganism in the present invention, any strains belonging to the genus *Sinorhizobium* capable of producing vitamin $B_6$ can be used, and a microorganism belonging to the genus *Sinorhizobium* may be isolated from natural sources, or may be purchased from culture collections. *S. meliloti* IFO 14782 (DSM 10226) is preferable to the present invention. A microorganism capable of producing large amount of vitamin $B_6$ can be constructed as described below.

(1) Preparation of *S. meliloti* IFO 14782 Harboring Recombinant Plasmid with pdxJ Gene

[A] Construction of Expression Plasmid for pdxJ

"pdxJ" referred to herein means the gene encoding an enzyme catalyzing synthesis of pyridoxol 5'-phosphate from 1-deoxy-D-xylulose 5-phosphate and aminoacetone 3-phosphate. A pdxJ gene derived from microorganism belonging to the genus *Sinorhizobium* is preferable. For example, a DNA of pdxJ derived from *S. meliloti* IFO 14782 can be cloned in the following manner. The primers for polymerase chain reaction (referred to as PCR hereinafter) are synthesized in accordance with the DNA sequence of pdxJ in a DNA data-base of *S. meliloti* strain 1021, and which contain restriction enzyme recognition site at the 5' end of each primer. The pdxJ gene can be amplified by PCR using the primers and chromosomal DNA of *S. meliloti* IFO 14782. Amplified pdxJ is ligated into a vector replicable in *Escherichia coli* such as available pUC series or pBR series. A plasmid, wherein pdxJ is inserted, can be selected by agarose gel analysis of the plasmid digested with endonuclease, and the sequence of amplified region can be ascertained with a DNA sequencer.

As a vector for expression of PdxJ protein in *E. coli*, a vector can be remodeled into a new plasmid, which has a promoter functioning in *E. coli* such as ptac, ptrp, plac, or ptrc followed by restriction enzyme recognition sequence. A plasmid expressing the PdxJ protein in *E. coli* can be provided by inserting the thus-obtained pdxJ into a thus-obtained expression plasmid, which encodes pdxJ under control of a promoter.

As a vector for expression of PdxJ protein in *S. meliloti*, a broad-host range vector, such as pVK100, pRK290, pLAFR1 or RSF1010, can be used. A plasmid expressing PdxJ protein in *S. meliloti* can be provided by inserting a DNA fragment encoding a promoter functioning in *S. meliloti*, such as ptac, plac, ptrc, pS1 (promoter of small ribosomal subunit of *S. meliloti*), or pNm (promoter of neomycin resistant gene) and pdxJ into a broad-host range vector.

The procedure for constructing recombinant vectors can be performed according to standard techniques known in the fields of molecular biology, bioengineering, and genetic engineering.

[B] Introduction of Recombinant Plasmid with pdxJ into *S. meliloti* IFO 14782

A plasmid encoding pdxJ of *S. meliloti* can be transformed to *E. coli* according to standard techniques known in the fields of molecular biology, bioengineering, and genetic engineering.

A broad-host range plasmid encoding pdxJ can be introduced into *S. meliloti* IFO 14782 by tri-parental mating in the following manner. *S. meliloti* as a recipient strain, *E. coli* harboring helper plasmid as a helper strain, and *E. coli* harboring donor plasmid as a donor strain are cultivated separately and mixed together. After mixed cultivation on plate, *S. meliloti* receiving a recombinant plasmid can be selected on agar plate containing appropriate antibiotics. The plasmids of colonies grown on the plates are examined by endonuclease digestion.

(2) Preparation of Mutant Endowed with Amino Acid Requirement Induced by Mutagenesis with N-methyl-N'-nitro-N-nitrosoguanidine (referred to as NTG hereinafter)

Pyridoxol in *S. meliloti* IFO 14782 is known to be synthesized by ring closure of two precursors, 1-deoxy-D-xylulose and 4-hydroxy-L-threonine [Tazoe et al., *J. Biol. Chem.* 275:11300-11305 (2000)]. In general, accumulation of amino acids synthesized by a branched pathway is reported to be greatly enhanced by induction of amino acid requirement. Thus it is conceivable to isolate amino acid requiring mutants to get higher vitamin $B_6$ producer. *S. meliloti* IFO 14782/pVKP601 prepared in (1) [B] is subjected to NTG mutagenesis to produce mutants producing pyridoxol more in the culture broth by induction of amino acid requiring mutants. *Sinorhizobium (Ensifer) meliloti* IFO 14782/pVKP601 was deposited on Feb. 29, 2008 under deposit number DSM 21235 at the DSMZ (Deutsche Sammlung von Mikroorganismen und Zeikulturen GmbH), Inhoffenstraße 7 B, 38124 Braunschweig, Germany under the provisions of the Budapest Treaty. Cells of the strain are treated with NTG. After treatment, a restorative cultivation is carried out and the resulting culture is plated out on agar medium. To isolate mutants requiring amino acid, the growth of colonies is tested on agar of inorganic nitrogen salt medium containing vitamins and nucleic acids. From the test, colonies requiring amino acid can be selected, and a vitamin $B_6$ high producer may be selected by testing productivity of vitamin $B_6$ in the fermentation. The strain *S. meliloti* PY-C341-K1 is one of the objective mutants in this present invention. *Sinorhizobium (Ensifer) meliloti* PY-C341-K1 was deposited on Feb. 29, 2008 under deposit No. DSM 21236 at the DSMZ (Deutsche Sammlung von Mikroorganismen und Zeikulturen GmbH), Inhoffenstraβe 7 B, 38124 Braunschweig, Germany under the provisions of the Budapest Treaty.

(3) Preparation of Mutants Endowed with Glycine Resistance Induced by Mutagenesis with NTG Biosynthesis of vitamin $B_6$ in *S. meliloti* IFO 14782 is well-known as described in (2). Pyridoxol is synthesized from a sugar and an amino acid precursors, and the latter precursor is from glycolaldehyde and glycine. Glycine is not only one of vitamin $B_6$ precursors but also a strong inhibitor to the growth of the strain. Accordingly, induction of glycine resistant mutant leads to enhancement of production of vitamin $B_6$. To isolate glycine resistant mutants, minimal inhibitory concentration of glycine against the strain should be examined on an appropriate medium because the inhibition strength was different in tested medium. Thus, strain PY-C341-K1 obtained in (2) is subjected to NTG mutagenesis to produce glycine resistant mutants. Cells of the strain are treated with NTG in a similar manner as described in (2). After treatment, a restorative cultivation is carried out and the resulting culture is plated out on an agar medium. To isolate glycine resistant mutants, the cell suspension is spread onto plates of agar medium containing appropriate concentration of glycine. After incubation, colonies resistant to glycine may be selected on agar medium containing glycine.

The microorganisms obtained in the present invention are incubated in a medium containing an assimilable carbon source, a digestible nitrogen source, an inorganic salt, and other nutrients necessary for their growth. As a carbon source, for example, glucose, fructose, lactose, maltose, galactose, sucrose, starch, dextrin, or glycerol may be employed. As a nitrogen source, for example, peptone, corn steep liquor, soybean powder, yeast extract, meat extract, ammonium chloride, ammonium sulfate, ammonium nitrate, urea, or their mixture thereof may be employed. Further, for trace elements, sulfates, hydrochlorides, or phosphates of calcium, magnesium, zinc, manganese, cobalt, and iron may be employed. And, if necessary, conventional nutrient factors, a trapping agent of phosphate ion, or an antifoaming agent, such as magnesium carbonate, aluminum oxide, allophane, animal oil, vegetable oil, or mineral oil can also be added supplementary in a fermentation medium.

The pH of the culture medium may be about 5.0 to 9.0, preferably 6.5 to 7.5. The cultivation temperature may be about 10° C. to 40° C., preferably 25° C. to 35° C. The cultivation time may be about 1 day to 15 days, preferably 2 days to 9 days.

In the cultivation, aeration and agitation usually give favorable results.

After the cultivation, vitamin $B_6$ produced also may be separated from the culture broth and purified. For this purpose a process generally used for extracting a certain product from the culture broth may be applied by utilizing various properties of vitamin $B_6$. Thus, for example, the cells are removed from the culture broth, the desired substance in the filtrate is absorbed on active carbon, then eluted and purified further with an ion exchange resin. Alternatively, the culture filtrate is applied directly to an ion exchange resin and, after the elution, the desired product is recrystallized from mixture of alcohol and water.

The microorganisms used in the present invention include all the mutant strains of genus *Sinorhizobium* capable of producing vitamin $B_6$ having a recombinant plasmid with pdxJ gene that acquired phenotypic property of histidine requirement, or glycine resistance, or combination of their phenotypic properties thereof. Among the strains of genus *Sinorhizobium*, a particularly preferred strain is *S. meliloti* PY-EGC1, which was deposited on Sep. 17, 2002 under deposit number DSM15209 at the DSMZ (Deutsche Sammlung von Mikroorganismen und Zeilkulturen GmbH) in Göttingen (Germany) under the Budapest Treaty.

The present invention will be explained more in detail by referring to the following examples; however, it should be understood that the present invention is not limited to those particular examples.

In the Examples, the amount of vitamin $B_6$ produced in culture broth can be assayed by the turbidity method with *Saccharomyces carlsbergensis* ATCC 9080 [Osbone and Voogt, The Analysis of Nutrients in Foods, Academic Press, London, 224-227 (1978)], and vitamin $B_6$ derivatives such as pyridoxol, pyridoxal, and pyridoxamine in a fermentation broth can be separately quantified by high pressure liquid chromatography (referred to as HPLC hereinafter).

EXAMPLE 1

Preparation of *S. meliloti* IFO 14782/pVK601

(1) Cloning of pdxJ of *S. meliloti* IFO14782

To amplify pdxJ of *S. meliloti* IFO 14782 using PCR method, the following two primers were synthesized according to the DNA sequence of pdxJ (2249854-2250606, complement) in the genome database of *S. meliloti* strain 1021 (Accession No. NC_003047): primer A (SEQ ID NO:1) with restriction enzyme NdeI recognition sequence including start codon of pdxJ and primer B (SEQ ID NO:2) with PstI site just after stop codon of pdxJ. Chromosomal DNA was extracted from the cells grown in a medium (referred to as LBMC hereinafter) composed of 1% Bacto Tryptone (Becton Dickinson Microbiology systems, MD, USA), 0.5% Bacto Yeast extract (Becton Dickinson Microbiology systems, MD, USA), 0.5% NaCl, 0.061% $MgSO_4.7H_2O$, and 0.036% $CaCl_2.2H_2O$ with QIAGEN genomic-tips (QIAGEN GmbH, Germany).

PCR was performed using advantage-HF PCR kit (CLONTECH Laboratories, Inc. CA, USA). 100 µl of reaction mixture contained 10 ng of chromosomal DNA of *S. meliloti* IFO 14782, 50 pmol of the two primers, 10 µl of 10× HF dNTP mix, 10 µl of appended 10× HF PCR reaction buffer, and 2 µl of 50× advantage-HF polymerase mix. The reaction conditions were as follows; holding at 94° C. for 3 min., 4 cycles of 30 sec at 98° C., 1 min at 53° C., 1 min at 72° C., 20 cycles of 30 sec at 98° C., 1 min 68° C., and holding at 72° C. for 10 min. 10 µl of reaction mixture was subjected to agarose gel on 1% (w/v) gels, and a DNA band of 770 bp was recovered from the gel with QIAEXII (QIAGEN GmbH, Germany). The fragment was ligated to pUC18, which was digested with SmaI and dephosphorylated with alkaline phosphatase, by SureClone ligation kit (Amersham Biosciences Corp., NJ, U.S.A.).

The thus obtained ligation mixture was transformed into *E. coli* JM109 competent cells (Takara Bio Inc., Shiga, Japan) and plated on plates of a medium composed of 1% Bacto Tryptone, 0.5% Bacto Yeast extract, and 0.5% NaCl (referred to as LB hereinafter) containing 100 µg/ml of ampicillin (referred to as Amp). Plasmids of colonies grown on the plates were prepared with Automatic DNA Isolation System PI-50 (Kurabo Industry Ltd., Japan). By analysis of the plasmid with restriction enzyme, a recombinant plasmid pSHT56, wherein pdxJ was the same direction as lacZ gene on pUC18, was obtained. pSHT56 was prepared from *E coli* JM109 harboring pSHT56 with QIAGEN plasmid Midi kit (QIAGEN GmbH, Germany). The DNA sequence of pdxJ in the plasmid was ascertained with an ALF DNA sequencer (Amersham Biosciences Corp., NJ, U.S.A.) and it was identical with that of a genome database of *S. meliloti* strain 1021.

As a vector for expression of pdxJ in *E. coli*, pUC 18 was remodeled into pUC-trc2, which has trc promoter region of pTrc99A (Amersham Biosciences Corp., NJ, USA) followed by NdeI recognition sequence. pUC-trc2 was prepared from *E. coli* JM109 harboring pUC-trc2 with QIAGEN plasmid Midi kit. To give an expression plasmid for pdxJ in *E. coli*, pUC-trc2 was digested with NdeI, and a 2.5-kb fragment was recovered from agarose gel and dephosphorylated with alkaline phosphatase (Takara Bio Inc., Shiga, Japan). On the other hand, pSHT56 was cleaved with NdeI, subjected to agarose gel and resulting 1-kb fragment was recovered from the gel with QIAEXII. The recovered 1-kb fragment was ligated to prescribed 2.5-kb fragment of pUC-trc2 with ligation kit (Takara Bio Inc., Shiga, Japan). *E. coli* JM109 was transformed with thus-obtained ligation mixture and plated on LB plates containing 100 µg/ml of Amp. Plasmid of a colony grown on the plate was prepared with Automatic DNA Isolation System PI-50. By analysis of the plasmid with restriction enzyme, a recombinant plasmid pSHT57, wherein pdxJ was the same direction as trc promoter, was obtained (FIG. 1). pSHT57 was prepared from *E. coli* JM109 harboring pSHT57 with QIAGEN plasmid Midi kit.

(2) Construction of Expression Plasmid for pdxJ in *S. meliloti* IFO 14782

To construct an expression vector in *S. meliloti* IFO 14782, pVK100 was used, which is reported to be a broad host range vector, IncP-1 type, and replicable in *S. meliloti*. pVK100 was prepared from *E. coli* HB101/pVK100 with QIAGEN plasmid midi kit, and digested with HindIII, blunt-ended by blunting kit (Takara Bio Inc., Shiga, Japan) and dephosphorylated with alkaline phosphatase. pSHT57 was digested with BamHI and KpnI. Resulting 875-bp fragment, which contained trc promoter and pdxJ, was recovered from agarose gel, blunt-ended by blunting kit, and ligated to prescribed pVK100 with ligation kit. *E. coli* HB101 competent cells (Takara Bio Inc., Shiga, Japan) was transformed with the obtained ligation mixture and plated on LB plates containing 10 µg/ml of tetracycline (referred to as Tc hereinafter). Plasmids of colonies grown on the plates were prepared with Automatic DNA Isolation System PI-50. By analysis of the plasmid with restriction enzyme, a recombinant plasmid, pVIK601, wherein trc promoter and pdxJ were the opposite direction against kanamycin resistant gene on, was obtained (FIG. 1).

(3) Complementing *E. coli* AT3208, pdxJ Mutant pSHT57 was transformed into pdxJ mutant, *E. coli* AT3208 (purchased from *E. coli* Genetic Stock Center, Yale Univ., U.S.A.). All Amp resistant transformants grew on vitamin $B_6$-free EMM plate composed of 10 g of glucose, 8 g of vitamin-free casamino acid (Becton Dickinson Microbiology systems, MD, U.S.A.), 2.5 mg of $MnSO_4 \cdot 5H_2O$, 125 mg of $MgSO_4 \cdot 7H_2O$, 125 mg of $CaCl_2 \cdot 2H_2O$, 425 mg of KCl, 250 µg $FeCl_3 \cdot 6H_2O$, 250 µg of thiamin hydrochloride, 8 µg of biotin, 15 g of Bacto agar (Becton Dickinson Microbiology systems, MD, U.S.A.) per liter (pH 6.8) whereas pdxJ mutant, *E. coli* AT3208, did not grow on the plate. This indicated that cloned pdxJ worked as PdxJ.

(4) Introduction of pVK601 into *S. meliloti* IFO 14782 pVK601 was introduced into *S. meliloti* IFO14782 by tri-parental mating as described below. *S. meliloti* IFO14782 as a recipient strain was inoculated in 5 ml of liquid LBMC medium and incubated with shaking at 30° C. at 140 rpm for 16 hours. 400 µl of the culture were transferred into the fresh same medium and incubated further for 6 hours. *E. coli* HB101 harboring pRK2013 ($Km^r$; IncP $tra^+$, ColEI ori) (ATCC 37159) as a helper strain was inoculated in 5 ml of liquid LB medium containing 50 µg/ml of kanamycin and incubated with shaking at 37° C. at 140 rpm for 16 hours. 100 µl of the culture were transferred into the fresh same medium and incubated further for 6 hours. *E. coli* HB101 harboring pVK601 was inoculated in 5 ml of liquid LB medium containing 10 µg/ml of Tc and incubated with shaking at 37° C. at 140 rpm for 16 hours. 100 µl of the culture were transferred into the fresh same medium and incubated further for 6 hours. Each strain was harvested and cells were mixed at 1:1:4 (v/v/v) ratio. The mixture was put on a nitrocellulose filter placed on LBMC agar plate. After this plate was incubated for 20 hours at 30° C., cells on the filter were scratched and suspended in sterilized 0.85% NaCl solution. The suspension was diluted appropriately and spread on LBMC plates containing 20 µg/ml nalidixic acid (to select for *S. melilot* IFO14782) and 10 µg/ml Tc (to select for pVK601). After incubation of these plates at 30° C. for 5 days, colonies grown on the plates were picked up and cultured for plasmid extraction by QIAGEN plasmid mini kit (QIAGEN GmbH, Germany). Thus-obtained plasmid DNA with treatment of endonuclease showed an identical pattern to pVK601 on agarose gel. From this result, one colony in the tested colonies was selected as *S. meliloti* IFO 14782/pVK601.

EXAMPLE 2

A loopful of *S. meliloti* IFO14782/pVK601 and the parent, *S. meliloti* IFO14782, grown on a LBMC agar plate at 30° C. for 48 hours was inoculated to tubes containing 8 ml of a seed medium (referred to as SM hereinafter) composed of 1% glucose, 1% corn steep liquor (Oji Cornstarch Co., Ltd., Tokyo, Japan), 0.2% Bacto yeast extract, 0.05% $MgSO_4 \cdot 7H_2O$, 0.001% $MnSO_4 \cdot 5H_2O$, and 0.001% $FeSO_4 \cdot 7H_2O$ (pH 7.0) and then the tubes were shaken on a reciprocal shaker (275 rpm) at 30° C. After shaking for 19 hours, each 4 ml of the cultures was transferred to a 500 ml flask with two baffles containing 200 ml of a production medium (referred to as PM hereinafter) composed of 6% glucose, 3% corn steep liquor, 0.8% Bacto yeast extract, 0.35% $NH_4Cl$, 0.05% $MgSO_4 \cdot 7H_2O$, 0.025% $MnSO_4 \cdot 5H_2O$, 1% Allophosite (Shinagawa Chemicals Co., Ltd., Tokyo, Japan) and 0.025% Actocol (pH 6.8) and shaken on a rotary shaker (180 rpm) at 30° C. After cultivation for 7 days, contents of vitamin $B_6$ in the supernatant of each culture broth were quantified by high pressure liquid chromatography (referred to as HPLC hereinafter) and produced vitamin $B_6$ was calculated by the internal standard method with 4'-deoxypyridoxol as described below. To prepare the samples for HPLC, 100 µl of the solution containing 100 mg/l of 4'-deoxypyridoxol as internal substance was added to 400 µl of the standard solutions of pyridoxol and the supernatant from the culture broth, and then the mixture was put on the following column. The analytical conditions were as follows: column, Capcell pak C18 SG120 (4.6×250 mm) (Shiseido Co., Ltd., Tokyo, Japan); mobile phase, 0.1 M sodium perchlorate, 0.1 M potassium phosphate, and 2% acetonitrile (pH 3.5); column temperature, 25-26° C.; flow rate, 1.0 ml/min; and detector, ultraviolet (UV) (at 292 nm). As a result, *S. meliloti* IFO14782/pVK601 produced 119 mg of pyridoxol per liter and was about 1.34 times higher than the parent, strain IFO 14782.

EXAMPLE 3

*S. meliloti* IFO14782/pVK601 obtained in Example 1 was cultured in a flask containing LBMCG containing 5 μg/ml of Tc for 17 hours at 30° C., and the cell suspension of the strain was prepared. A tube containing 5 ml of the reaction mixture composed of 150 μg/ml of NTG and $1.6 \times 10^9$ cells per ml in 50 mM Tris-HCl buffer (pH 8.0) was incubated with a reciprocal shaking (275 rpm) for 30 min at 30° C. The cells were washed twice with sterile saline and suspended in saline. 100 μl of the cell suspension was spread onto agar plates containing LBMCG containing 5 μg/ml of Tc, and then the plates were incubated for 2 days at 30° C. The cells grown on the plates were recovered in 7 ml of sterile saline, and the cell suspensions were serially diluted $10^{-1}$-$10^{-7}$ in sterile saline and spread onto the same agar plates. To isolate amino acid requiring mutants, the growth of 1,136 colonies grown on LBMCG containing 5 μg/ml of Tc were tested on agar of a minimum medium (referred to as MM hereinafter) composed of 1% glucose, 0.22% $NH_4Cl$, 0.06% $K_2HPO_4$, 0.06% $KH_2PO_4$, 0.04% $MgSO_4.7H_2O$, 0.02% $CaCl_2.2H_2O$, 0.04% NaCl, and the following metal salts, vitamins, and nucleic acids (per liter): 12 mg of $FeCl_3.6H_2O$, 4 mg of $MnSO_4.5H_2O$, 0.5 mg of $H_3BO_3$, 0.4 mg of $Na_2MoO_4$, 0.32 mg of $ZnSO_4.7H_2O$, 0.04 mg of $CuSO_4.5H_2O$, 0.002 mg of $CoCl_2.6H_2O$, 4 mg of calcium pantothenate, 3 mg of thiamin-HCl, 1.25 mg of riboflavine, 0.04 mg of biotin, 10 mg of hypoxanthine, 10 mg of guanine sulfate, 10 mg of thymine, and 10 mg of uracil containing 5 μg/ml of Tc. After incubation for 4 days at 30° C., 37 colonies indicating a poor or no growth were picked up to LBMCG agar containing 5 μg/ml of Tc, and the productivity of vitamin $B_6$ was examined by flask fermentation. One loopful cells of 37 colonies and *S. meliloti* IFO14782/pVK601 (parent) were inoculated to tubes containing 8 ml of SM medium, and then the tubes were shaken on a reciprocal shaker (275 rpm) at 30° C. After shaking for 19 hours, each 4 ml of culture broth was transferred to 500-ml flasks with two baffles containing 200 ml of PM medium and shaken on a rotary shaker (180 rpm) at 30° C. After cultivation for 7 days, contents of vitamin $B_6$ in the supernatant of each culture broth were quantified by HPLC. As a result, *S. meliloti* PY-C341K1 produced 171 mg of pyridoxol per liter and was 1.44 times higher than the parent, strain IFO14782/pVK601.

The amino acid requirement of strain PY-C341K1 together with the parent, strain IFO14782/pVK601, was examined by culturing for 2 days at 30° C. in tubes containing 8 ml of MM supplemented with various kinds of amino acids. From a result, strain PY-C341K1 grew as well as the parent, IFO14782/pVK601, in MM medium supplemented with 42 μg/ml of histidine.

EXAMPLE 4

In a similar manner as described in Example 3, *S. meliloti* PY-C341K1 was cultured in a flask containing LBMCG containing 10 μg/ml of Tc for 16 hours at 30° C., and the cell suspension of the strain was prepared. A tube containing 5 ml of the reaction mixtures composed of 0, 30, and 50 μg/ml of NTG and $1.6 \times 10^9$ cells per ml in 50 mM Tris-HCl buffer (pH 8.0) was incubated with a reciprocal shaking (275 rpm) for 30 min at 30° C. The cells of each reaction mixture were washed twice with sterile saline and suspended in saline. 100 μl of the cell suspension was spread onto agar plates containing LBMCG containing 10 μg/ml of Tc, and then the plates were incubated for 2-3 days at 30° C. The cells grown on the plates were recovered by suspending in sterile saline. After centrifugation of the suspension, the cell suspension was diluted to give a turbidity of $OD_{600}=1.6$, and finally to $10^{-5}$. Each 100 μl of the diluents was spread onto five agar plates containing LBMCG containing 10 μg/ml of Tc and 0, 0.125, 0.15, or 0.175% glycine because 0.15% glycine completely inhibited the growth of *S. meliloti* PY-C341K1 on LBMCG plate, and then the plates were incubated for 4 days at 30° C. Ten colonies treated with 50 μg/ml of NTG grown on plates LBMCG containing 10 μg/ml of Tc and 0.175% glycine were picked up on LBMCG agar containing 10 μg/ml of Tc. After incubation for 2 days at 30° C., the productivity of vitamin $B_6$ in ten colonies together with the parent strain (*S. meliloti* PY-C341K1) was examined by flask fermentation. One loopful cells was inoculated to tubes containing 8 ml of SM medium, and then the tubes were shaken on a reciprocal shaker (275 rpm) at 30° C. After shaking for 19 hours, each 4 ml of culture broth was transferred to a 500-ml flask with two baffles containing 200 ml of PM medium modified to 0.175% $NH_4Cl$, and shaken on a rotary shaker (180 rpm) at 30° C. After shaking for 4 days, sterile solution of urea was added to the each flask at 0.125%, and the shaking were further continued for 3 days. The contents of vitamin $B_6$ in the supernatant of 7-day culture broth were quantified by HPLC method as described in Example 3. As a result, *S. meliloti* PY-EGC1 produced 362 mg of pyridoxol per liter and was about 2.11 times higher than strain PY-341K1 (the parent).

EXAMPLE 5

Vitamin $B_6$ was recovered from the culture broth of *S. meliloti* PY-EGC1 prepared in the same cultural conditions as described in Example 5. Pyridoxol at each purification step and the concentration was followed by HPLC. One liter of the 168 hour-culture broth containing 344 mg/L of PN was centrifuged at 7,500 rpm for 10 min. The pH of the resultant supernatant was adjusted to 3.1 with 1N hydrochloric acid, and then the supernatant was applied to a column (5.5×15 cm) packed with 350 ml of Amberlite CG 120 ($H^+$ form, 100-200 mesh, Rohm and Haas Company, Philadelphia, Pa., USA). The column was washed with 500 ml of deionized water and then eluted with 5% ammonium hydroxide. The vitamin $B_6$ fractions were concentrated under reduced pressure. The residue thus obtained was dissolved in 10 ml of deionized water, and the solution was charged on a column (5.5×16 cm) packed with 380 ml of Dowex 1×4 ($OH^{31}$ form, 200-400 mesh, Dow Chemical Co., Ltd., Midland, Mich., U.S.A.), and then washed with 500 ml of deionized water. The column was then eluted with 0.1 N HCl. The fractions containing pyridoxol was concentrated to small volume under reduced pressure. After the solid residue was dissolved in small amount of hot ethanol, the solution was kept standing at 4° C. overnight. The resultant precipitates were collected by filtration and dried in vacuo to obtain 282 mg of crude crystals. It was recrystallized from ethanol to obtain 217 mg of white crystals having a melting point of 160° C. The infrared absorption, UV absorption, and NMR spectrum of the product of the product coincided with those of authentic pyridoxol.

Table 1 summarizes the vitamin $B_6$ productivities of *S. meliloti* IFO 14782 (DSM No. 10226), *S. meliloti* IFO 14782/pVK601, and their mutants so far obtained.

TABLE 1

Pyridoxol Productivities of S. meliloti IFO 14782 (DSM No. 10226), S. meliloti IFO 14782/pVK601, and their Mutants

| Example | Microorganism | Phenotypic properties | Pyridoxol (mg/L) | Magnitude of increasing |
|---|---|---|---|---|
| | S. meliloti IFO 14782 (DSM 10226) | | 89 | 1.0 |
| 2 | S. meliloti IFO 14782/pVKP601 | amplification of pdxJ | 119 | 1.34 |
| 3 | S. meliloti PY-C341K1 | histidine requirement | 171 | 1.92 |
| 4 | S. meliloti PY-EGC1 | glycine resistance | 362 | 4.07 |

The invention claimed is:

1. A mutant of a recombinant microorganism selected from the group consisting of Sinorhizobium meliloti IFO 14782/pVK601, Sinorhizobium meliloti PY-C341-K1, and Sinorhizobium meliloti PY-EGC1 capable of producing vitamin $B_6$ having a plasmid expressing a recombinant pyridoxol 5'-phosphate synthase polypeptide, said plasmid being selected from the group consisting of pVK100, pRK290, pLAFR1, and RSF1010 whereby the recombinant microorganism has acquired a phenotypic property of histidine requirement or glycine resistance, or a combination of the phenotypic properties thereof.

2. The mutant of a recombinant microorganism according to claim 1, wherein a polynucleotide sequence encoding said pyridoxol 5'-phosphate synthase polypeptide is cloned into plasmid pVK100.

3. The mutant of a recombinant microorganism according to claim 1 which is Sinorhizobium meliloti PY-EGC1.

4. A process for producing vitamin $B_6$ which comprises cultivating the mutant according to claim 1 in a cultivation medium at a pH value of about 5.0 to 9.0, at a temperature of 10° C. to 40° C., and for 1 day to 15 days under aerobic conditions, isolating vitamin $B_6$ from the cultivation medium.

5. The process according to claim 4, wherein the mutant is Sinorhizobium meliloti PY-EGC1.

6. The mutant of a recombinant microorganism according to claim 2, wherein a recombinant plasmid comprising the pyridoxol 5'-phosphate synthase gene is pVK601.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: Primer sequence A for pdxJ

<400> SEQUENCE: 1
tcccatatgc ctgcaaagct ctcc          24

<210> SEQ ID NO 2
<211> LENGTH: 24
<212> TYPE: DNA
<213> ORGANISM: Artificial
<220> FEATURE:
<223> OTHER INFORMATION: Primer sequence B for pdxJ

<400> SEQUENCE: 2
tccctgcagt taagccgtct cgcc          24